United States Patent [19]

Fernö et al.

[11] Patent Number: 4,579,858

[45] Date of Patent: Apr. 1, 1986

[54] SMOKING SUBSTITUTES FOR NASAL ADMINISTRATION-I

[75] Inventors: Ove B. Fernö ; Stig K. A. Helgertz; Corfitz B. I. Ohlsson, all of Helsingborg, Sweden

[73] Assignee: Aktiebolaget Leo, Helsingborg, Sweden

[21] Appl. No.: 570,001

[22] Filed: Jan. 11, 1984

[30] Foreign Application Priority Data

Jan. 21, 1983 [GB] United Kingdom ............... 8301659

[51] Int. Cl.$^4$ .......................................... A61K 31/465
[52] U.S. Cl. ................... 514/343; 131/270; 131/347; 131/352; 131/359
[58] Field of Search ............... 424/264; 131/270, 347, 131/352, 359; D24/63, 62; D28/91.1; 514/343

[56] References Cited

U.S. PATENT DOCUMENTS

| 865,026 | 9/1907 | Ellis | 131/270 |
|---|---|---|---|
| 2,346,362 | 4/1944 | Dolman | 424/264 |
| 2,836,329 | 5/1958 | Chenette | D24/63 |
| 3,069,314 | 12/1962 | Jenkins | 424/264 |
| 3,170,462 | 2/1965 | Hall | D24/63 |
| 3,171,446 | 3/1965 | Koch | D24/63 |
| 3,252,802 | 5/1966 | Cunningham | 424/264 |
| 3,368,567 | 2/1968 | Speer | 424/264 |
| 3,870,794 | 3/1975 | Hutchinson et al. | 424/264 |
| 4,117,850 | 10/1978 | Wood | 131/359 |
| 4,284,649 | 8/1981 | Wiczer | 424/362 |

FOREIGN PATENT DOCUMENTS

| 2428M | 3/1964 | France | 424/264 |
|---|---|---|---|
| 2486392 | 1/1982 | France | 424/362 |
| 57-32215 | 2/1982 | Japan | 424/362 |
| 58-134008 | 8/1983 | Japan | 424/264 |

Primary Examiner—Ronald W. Griffin
Attorney, Agent, or Firm—Gordon W. Hueschen

[57] ABSTRACT

A smoking substitute composition for application directly into the nose, consisting essentially of an aqueous solution of nicotine or a physiologically acceptable acid addition salt thereof, having a pH value of 2 to 6, containing 10 to 0.5% w/v of nicotine calculated as the free base, containing a nasally-acceptable thickening agent, and having a viscosity not less than 100 centipoise and optionally containing also a further ingredient selected from the group consisting of a nasally acceptable buffer, emulsifying agent, preservative, flavoring agent and antioxidant. A method of diminishing the desire of a subject to smoke comprising the step of administering to the subject a smoking substitute composition as set forth in the foregoing.

19 Claims, 11 Drawing Figures

SMOKING SUBSTITUTES FOR NASAL ADMINISTRATION-I

In the U.S. Surgeon General's 1979 report on Smoking and Health, it was estimated that in the U.S. alone about 350,000 deaths are caused each year by diseases related to cigarette smoking. In fact, excessive smoking is now recognized as one of the major health problems throughout the world. The most advantageous thing a heavy smoker can do is, therefore, to reduce or preferably even stop smoking completely. Experience shows, however, that most smokers find this extremely difficult. It is generally accepted that this difficulty results from the fact that heavy smokers are dependent on nicotine, which is considered to be one of the risk factors in tobacco smoke. The most important risk factors, however, are substances which are formed during the combustion of tobacco, such as carbon monoxide, tar products, aldehydes, and hydrocyanic acid.

One way to reduce smoking would, of course, be to provide nicotine in a form or manner other than by smoking. There are available tobacco products which can be used for this purpose, such as chewing tobacco and snuff, which latter material can be administered both via nasal and oral routes. Tobacco products of this type are, however, not without harmful effects, such as cancer, and are not well accepted socially. One already existing product, which fulfils the above-mentioned objective of providing nicotine in a less harmful and more socially-acceptable manner, is a nicotine chewing gum. Nicotine-containing chewing gums are not new. U.S. Pat. No. 865,026 and 940,521 are representative of ancient efforts along these lines. More recently, however, U.S. Pat. No. 3,877,468, 3,901,248, and 3,845,217 have appeared, and the products of the latter of these three patents are now being marketed on an international scale. These products combine a nicotine-containing cation exchange resin complex in gum base, preferably together with a buffering agent which maintains the pH of the saliva above its normal physiological pH. These compositions have met with considerable success but, of course, there are hardened smokers who cannot adapt to the substitution of nicotine-containing chewing gums for their usual smoking routine, and it is at least in part to those habitual smokers to which the present invention is directed. Another group of smokers to which the present invention is particularly directed are those with dentures, and for whom a chewing gum substitute is not suitable.

It seems particularly difficult to find other smoking substitutes equivalent to or as effective as the chewing gum substitutes just mentioned, and the aerosol compositions of the Gildermeister or Smith British Pat. Nos. 1,528,391 or 2,030,862, adapted tn be sprayed into the mouth of the user, are hardly an answer to the problem and in actuality appear to be merely a particular extension of a suggestion made as early as 1967 (A. Herxheimer et al, Lancet 1967, II 754–5).

Other compositions of nicotine have been suggested for various purposes. For example, Hutchinson et al in U.S. Pat. No. 3,870,794 have suggested the employment of certain nicotine compositions for the treatment of certain emotional disorders. However, Hutchinson et al in no way suggested any compositions suitable for attainment of the objectives of the present invention, nor did they suggest the mode of administration presently involved.

Unilever in German Offenlegungsschrift No. 2,313,996, published Oct. 10. 1974, describes certain water-soluble readily-absorbed snuff powders and a process for their manufacture, but these involve only extracts of tobacco aroma combined with solid water-soluble adsorbents. Such snuff substitutes are supposedly less prone to discolour teeth, fingers, and so on, but contribute nothing as far as the problem presently under consideration and certainly suggest no socially-acceptable solution with respect thereto.

One socially- and toxicologically-acceptable way of administering nicotine would be by way of the administration thereof directly into the nasal cavity in a manner and in a form not suffering from the socially-unacceptable aspects of snuff. However, before the present invention, no solution along these lines has existed and, to the best of our knowledge, none has been suggested previously. Several reasons or preconceptions speak against such a solution. Among these is the fact that nicotine has a very strong taste and smell, for which reason it has not seemed a priori feasible to apply nicotine directly into the nasal cavity. In the case of snuff, it will be understood that the nicotine is embodied in a matrix of tobacco from which it is released slowly upon contact with the nasal mucosa. This release and, accordingly also absorption of the nicotine into the blood, is sufficiently slow that absorption is in fact frequently accelerated by mixing the finely-ground snuff tobacco with additives, including substances such as potash or lime, to inrrease the pH and rate of absorption. If nicotine were itself to be administered directly to the nasal mucosa, it would of course not be accompanied by the tobacco matrix present in snuff and accordingly would not be characterized by the slow release and absorption of nicotine, as in snuff in the absence of pH-elevating ingredients. It is probable that, if any one prior to the present invention did attempt to administer nicotine directly to the nasal mucosa, whether in the form of aqueous solutions or otherwise, it was the extremely strong taste and smell, and above all the strong local sensations effected thereby, which doomed this approach toward development of an acceptable substitute for snuff or, as is an object of the present invention, a nasally-administerable substitute for smoking. Prior to the present invention, if any one ever thought of it, an approach to a smoking substitute which proceeeded along the lines of snuff has undoubtedly appeared to be predestined to failure, not only because of the total social unacceptability of snuff, but also because of the fact that snuff itself, quite apart from its social unacceptability, is not popular among users of tobacco in any form.

However, it has now surprisingly been found that the problem of providing a substitute for smoking can be solved by the provision and employment of a smoking substitute for application directly to the nasal mucosa in the form of an aqueous nicotine solution having certain defined limits of nicotine content, certain defined pH limits, and certain other characteristics which, when combined into an aqueous nicotine solution and method of treatment, provide not only the necessary nicotine for satisfaction of the subject and a socially-acceptable mode of administration, but also adequate tolerance on the part of the subject to whom the nicotine solution is nasally administered. Accordingly, a new and important solution to the long-standing problem of smoking has been found and is provided by the compositions and method of the present invention.

OBJECTS OF THE INVENTION

It is an object of the present invention to provide a novel smoking substitute which may be administered directly to the nasal mucosa. It is a further object to provide such a smoking substitute in the form of an aqueous nicotine-containing solution. It is another object of the invention to provide such nicotine-containing aqueous solution having certain prescribed characteristics of nicotine content, pH, viscosity, and volume, individually and in combination, thereby to provide a novel nasally-administerable smoking substitute composition for use in the treatment of subjects requiring the same or desiring to break the smoking habit. Still an additional object of the present invention is to provide a method of administering nicotine to a subject as a smoking substitute which involves the direct administration of an aqueous solution of nicotine into the nasal passageway. Other objects of the invention will become apparent hereinafter as the disclosure proceeds, and still other objects of the invention will be apparent to one skilled in the art.

SUMMARY OF THE INVENTION

In summary, the invention comprises the following:

A smoking substitute composition for application directly into the nose, consisting essentially of an aqueous solution of nicotine or a physiologically-acceptable acid addition salt thereof, having a pH-value of 2 to 6, containing 10 to 0.5% w/v of nicotine calculated as the free base, containing a nasally-acceptable thickening agent, and having a viscosity not less than 100 cp and optionally containing also a further ingredient selected from the group consisting of a nasally acceptable buffer, emulsifying agent, preservative, flavoring agent and antioxidant.

A specific aspect of the invention concerns a smoking substitute composition for application directly into the nose, consisting essentially of 0.05 up to 0.5 ml of an aqueous solution of nicotine or a physiologically-acceptable acid addition salt thereof, having a pH-value of 2 to 6, containing 10 to 0.5% w/v of nicotine calculated as the free base, containing a nasally-acceptable thickening agent, and having a viscosity not less than 100 cp (centipoise), in the form of a dosage unit which delivers about 0.5 to 5 mg nicotine per unit dose, especially 1–4 mg nicotine per unit dose; preferably having a viscosity not less than 1000 cp; especially about 3000–4000 cp; preferably containing an effective amount of a nasally-acceptable buffer having a buffering effect in the range of pH 2 to 6; preferably in the range of pH 4 to 6; preferably wherein the thickening agent is a nasally-acceptable natural, semi-synthetic, or synthetic polymer; or wherein the thickening agent is a nasally-acceptable oily substance constituting the oil-phase of an emulsion; preferably such a composition also comprising an emulsifying agent; especially having a pH-value of 3 to 5; especially such a composition containing 5 to 1% w/v of nicotine; particularly such a composition containing 4 to 2% w/v of nicotine; preferably having a volume of from 0.05, e.g. at least 0.1 up to 0.3 ml and preferably having a viscosity not higher than 6000 cp; such composition may also contain an effective amount of a nasally-acceptable preservative; such composition may also contain an effective amount of a nasally-acceptable flavour; and such composition may also contain an effective amount of a nasally-acceptable antioxidant, particularly such composition wherein the composition is in unit dosage form in a plastic container having a nostril-insertable neck portion of restricted volume adjacent to an emission opening and a pressure-application chamber of relatively larger volume in communication with said neck portion, and wherein the said composition is disposed in said neck portion and of sufficient viscosity to retain said location until the time of application; or in a container having a nostril-insertable container neck dimensioned so as to contain a unit-dose and wherein a squeeze-bottle container constitutes the relatively larger pressure-application chamber, the unit-dose neck thus constituting a portion of a multi-dose container.

Another aspect of the invention concerns a method of administering a smoking substitute composition to a subject for purposes of diminishing the desire of the subject to smoke and thereby assist the subject to break the smoking habit, which comprises the step of administering to the subject intranasally a smoking substitute composition as disclosed above.

SPECIFIC REFERENCE TO THE DRAWINGS

Figures 1, 3:
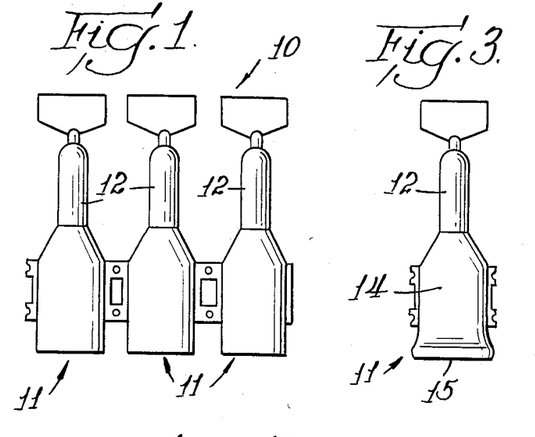
FIG. 1 is a plan view of a unit-dose plastic container which may be employed to contain the composition of the invention, in its usual form as prepared in multiple from a plastic moulding process, ends being open.
FIG. 3 is a plan view of a unit-dose container which may be employed to contain the composition of the invention, closed at its end and filled with the composition of the invention.
Figures 2, 6, 7, 8:
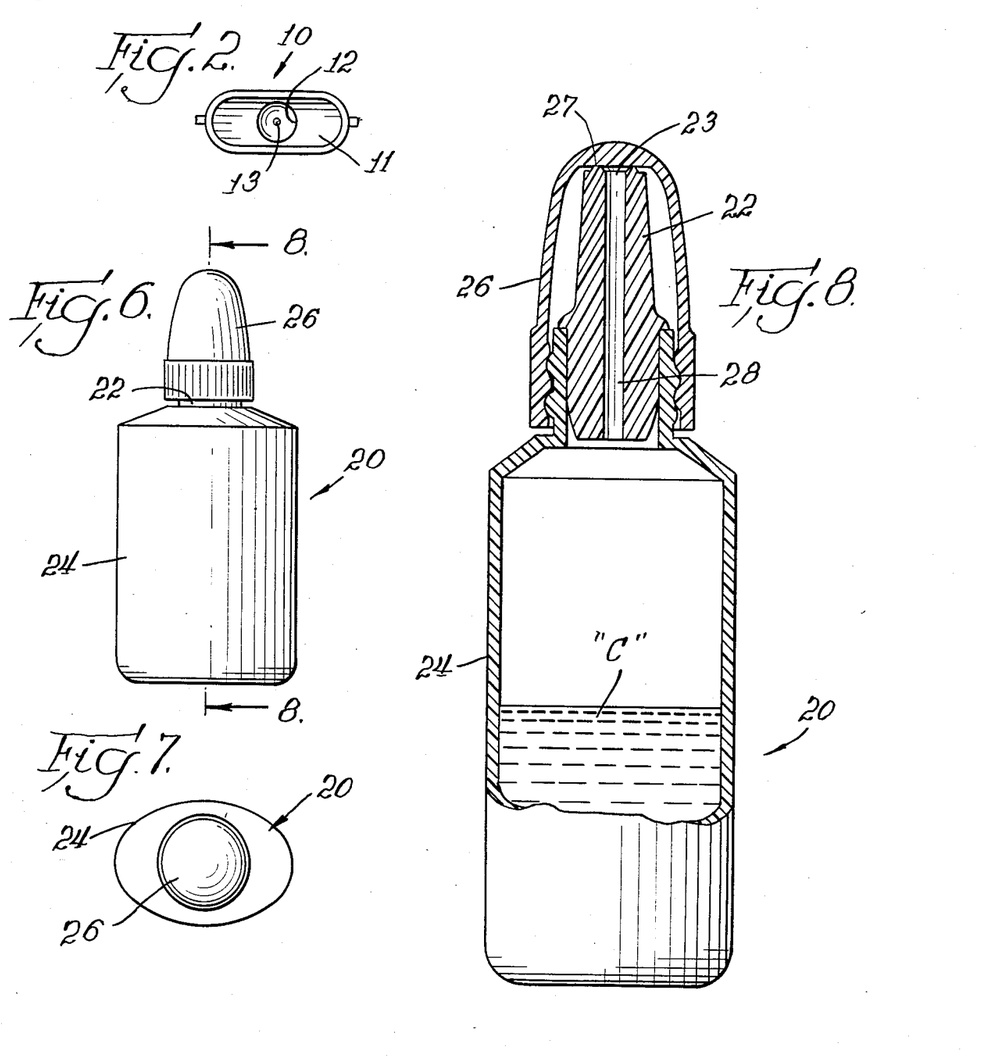
FIG. 2 is a bottom view of a single container of FIG. 1.
FIG. 6 is a plan view of a squeeze-bottle container which may be employed to contain the composition of the invention, having a neck which is adapted to deliver a unit-dose of a composition according to the invention, with cap in place.
FIG. 7 is a top view of the container of FIG. 6.
FIG. 8 is a side view of the container of FIG. 6, partially in section along line 8—8 of FIG. 6.
Figures 4, 5:
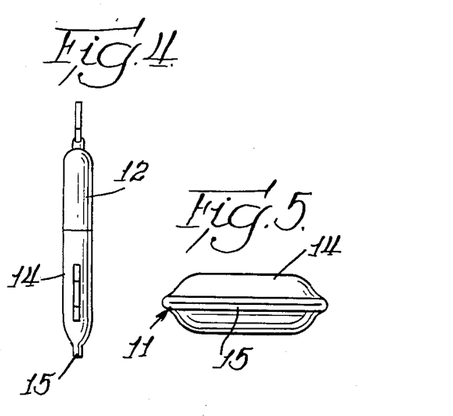
FIG. 4 is a side view of the container of FIG. 3.
FIG. 5 is an end view of the container of FIG. 3.

Referring now to the drawings, wherein all the significant parts are numbered and wherein the same numbers are used for the same parts throughout, the same elements in different embodiments differing by a factor of 10, FIG. 1 shows at 10 a unit dose container in multiple as prepared by a molding process, with the end thereof being open at its bottom 11. FIG. 2 shows a bottom view of a unit dose container, separated from the multiple arrangement shown in FIG. 1. The unit dose container is shown at 10, its open bottom 11, neck 12, and emission orifice 13 being visible. These same elements are visible in FIGS. 3, 4 and 5, wherein the pressure chamber 14 of the unit dose container 10 is indicated, as well as the heat and pressure seal 15 employed for closing the bottom 11.

In FIG. 6 is shown a second embodiment, being a multi-dose squeeze bottle container, shown at 20, having pressure chamber 24, neck 22, and cap 26. The same elements are shown in FIGS. 7 and 8, which latter Fig. shows composition "C" interior of the pressure chamber 24, emission orifice 23, raised rib 27 for sealing against the inside of cap 26, and passage 28 having a diameter in proportion to the viscosity of the composition "C" and the amount of dosage desired.

Figures 9, 10, 11:
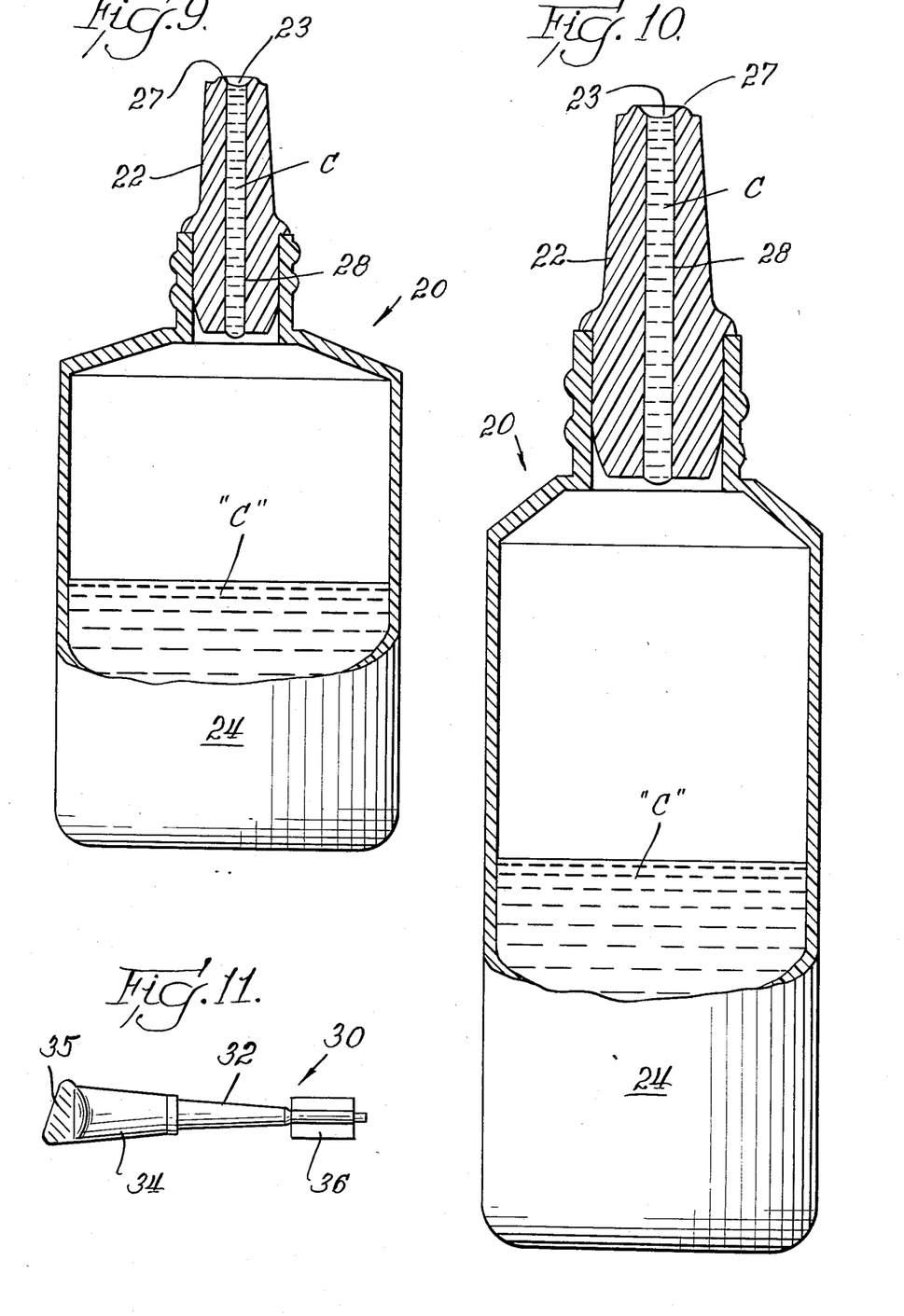
FIG. 9 is a front view of the container of FIG. 6 with cap removed, partially in section, showing composition adhering to the neck.
FIG. 10 is a side view of the container of FIG. 6 with cap removed, partially in section, showing composition adhering to the neck.
FIG. 11 is a plan view of another type of unit-dose container which may be employed to contain a composition of the invention.

FIGS. 9 and 10 show the same elements, but also illustrate composition "C" adhering within passage 28 in neck 22 of the container.

FIG. 11 shows another unit-dose container constituting a further embodiment of the invention at 30, with pressure chamber 34 having seal 35 at its one end and neck 32 closed by cap 36 at its other end.

In FIG. 1, an open-end unit-dose container of material such as polyethylene, polypropylene, polystyrene, or the like, suitable for use according to the present invention is shown as it comes in multiple form from the usual plastic mould. This multiple moulding is separated into individual containers, such as shown in FIG. 3. The containers are filled with a composition of the invention through the bottom end thereof, and the end is closed by application of heat and pressure, to provide the filled unit-dose container. According to the invention, such container advantageously includes a unit-dose neck-portion, adjacent an emission opening in communication with a relatively enlarged pressure-application chamber. For purposes of assisting the composition to remain in the unit-dose neck-portion of the container, especially when the composition has minimal viscosity, the passageway between the pressure-application chamber and the neck-portion may be, and frequently is, partially obstructed with a bead or ring, or a series of inwardly-extending protuberances or fingers, usually located at the juncture between the pressure-application chamber and the neck-portion. Upon application of pressure to the pressure-application chamber of the unit-dose container, the unit dosage of the composition of the invention which, as shown, is of viscosity sufficient so that it clings to the unit-dose neck-portion of the unit-dose container, is ejected through the emission orifice into the nasal passageway of the subject.

In FIG. 6 is shown a multi-dose squeeze-bottle container, suitable for use in accord with the present invention. This embodies a neck-portion adapted to contain a unit-dose so that, upon tipping the container to an upside-down vertical position, the unit-dose neck-portion fills with composition according to the invention. Upon return of the container to an upright position, the composition is of viscosity sufficient to adhere to the unit-dose neck-portion of the container. For purposes of assisting the composition to remain in the unit-dose neck-portion of the container, especially when the composition has minimal viscosity, the passageway between the pressure-application chamber and the neck-portion may be partially obstructed with a bead or ring, or a series of inwardly-extending protuberances or fingers, usually located at the juncture between the pressure-application chamber and the neck-portion. Upon administration of pressure to the pressure-application chamber of the squeeze-bottle in the usual manner, the unit-dose of composition is administered through the orifice at the end of the unit-dose neck-portion of the squeeze-bottle directly into the nasal passageway of the subject. With compositions of very high viscosities, it is advantageous to include a small capillary or hole in the cap just above the emission orifice for purposes of permitting a single squeeze of the squeeze-bottle to fill the unit-dosage neck with desired composition, prior to removal of the cap and administration thereof into the nasal passageway. Many different unit-dose forms or multiple-dose forms of containers having a unit-dose neck-portion may be employed with equal facility, and the unit-dose containers or multiple-dose containers having a unit-dose neck-portion are given here only by way of illustration and not by way of limitation, as will be immediately apparent to any one skilled in the art.

GENERAL DESCRIPTION OF THE INVENTION

Although it is not desired to be limited to any theory of the invention, or why it is physiologically tolerable by a subject upon whom it is employed, it is believed that maintenance of the prescribed pH-range according to the invention provides the nicotine ion in the form of a salt thereof, rather than in the form of the free base, which at normal physiological pH's of 7 or thereabouts is intolerable on administration to the mucous membrane. At a pH of 7 or above, more than 10% of the nicotine content is in the form of the free base, and absorption is so rapid that untoward physiological effects are observed, frequently of a serious nature. Strong local sensations, such as burning, intensive sneezing, and the like, are often experienced. However, with maintenance of the pH-ranges according to the invention, i. e., about 2–6, untoward sensations and physiological reactions are infrequently encountered, and are of a much less aggravating nature. This is believed to be due to the fact that the absorption of nicotine into the system in the protonated form, i.e., as its salt, occurs much more slowly than when the nicotine is in the unprotonated form, i.e., as the free base. According to this theory of the invention, the physiological pH of the mucous membrane results in a conversion of the salt to the free base at a slow rate, so that excessive amounts are not present in contact with the nasal mucosa. As the salt is slowly converted to the free base by the physiological pH of the nasal mucosa, small amounts which can be tolerated by the subject are made available for absorption. Accordingly, maintenance of the pH-ranges in the aqueous nicotine compositions of the invention within the prescribed ranges is critical and is of the essence of the invention.

In general, then, the present invention involves aqueous nicotine compositions which are suitable for administration directly to the nasal mucosa of the subject, and a method of administering nicotine to a subject as a substitute for smoking comprising the step of applying directly to the nasal mucosa in the nasal cavity such a physiologically-acceptable aqueous nicotine composition as just described.

According to the broader principles of the invention, the volume of the composition in a unit-dose should consist essentially of 0.05 up to 0.5 ml of the aqueous solution of nicotine or physiologically-acceptable acid addition salt thereof, the pH-value should be between 2 and 6, and the composition should contain 10% down to about 0.5% weight per volume of nicotine calculated as the free base, and the viscosity of the composition should be not less than about 100 cp. This viscosity can be conveniently obtained by the employment of physiologically- and nasally-acceptable thickening agents, as will be discussed further hereinafter. Single dose units according to the invention should deliver about 0.5–5 mg of nicotine per unit-dose, and this is a simple relationship readily effected between the concentration of the nicotine solution and the amount administered, as will be readily apparent to one skilled in the art.

By way of further explanation, at a pH of about 6, only about 1% of the nicotine is in the free base form, whereas the remainder of the nicotine is in the form of nicotinium ion, i.e., in the form of a salt with whatever acid may be employed to effect the prescribed pH-range of the composition of the invention. As the pH is decreased, even less of the nicotine is in the form of the free base, substantially all of the nicotine being in the form of nicotinium ions at the lower pH values. According to the Merck Index, 9th ed., the pH of an 0.05 molar solution of nicotine is 10.2. Thus, nicotine free base is indeed a base and, without adjustment of pH, a solution of free basic nicotine is not only outside the scope of the invention but also unsuitable for use according to the present invention.

According to the invention, either natural or synthetic nicotine may be employed, or a pharmacologically-acceptable salt thereof. Natural nicotine, as it exists in tobacco, is preferred. Pharmacologically-acceptable salts include, for example, nicotine hydrogen tartrate, nicotine tartrate, nicotine hydrochloride, nicotine dihydrochloride, nicotine sulphate, and so forth. Many such salts are known.

Further, according to the invention, an acidid pH is maintained in the compositions of the invention. For maintenance of a pH within the prescribed range, in addition to buffers which may be employed as further disclosed hereinafter, the employment of an acid, preferably an acid of the type just mentioned or citric acid, lactic acid, succinic acid, phosphoric acid, or similar pharmacologically-acceptable acids, for salt formation with the nicotine, may be employed. When the salt itself is not properly within the pH-range, modification may be effected in the usual manner by employment of an acid, a base, or a buffer.

With respect to the volume of solution employed in unit-dose form, it should go without saying that this volume should be sufficient to enter the nasal cavity and maintain contact with the nasal mucosa for a period sufficient for absorption thereof into the bloodstream of the subject, but should not be of such an amount that excessive run-off occurs. Obviously, the amount should not be so great that substantial quantities of the solution run down into the throat of the user, since this is not the object of the invention and untoward side-effects and diminished tolerability always result upon exposure of the buccal cavity to the compositions of the invention. Accordingly, it is not desired that the compositions enter into contact with the buccal cavity and the volume of the composition employed in a unit-dose, and in a unit-dose treatment of a subject, according to this invention should be such that contact with the buccal cavity does not occur.

Moreover, the amount of nicotine in the solution should not vary substantially from the defined 10–0.5 weight/volume per cent of nicotine. The per cent weight/volume of nicotine has been stated as being between 10–0.5, on a diminishing scale, in contrast to the statement of the volume in an ascending order, i.e., 0.05 up to 0.5 ml, to emphasize the fact that an objective is to obtain an effective amount of nicotine per unit-dose, i.e., between 0.5 and 5 mg, preferably 1–4 mg, of nicotine per unit-dose. This is readily accomplished by employing a selected volume and a relative weight-/volume concentration of nicotine, as will of course be readily appreciated by one skilled in the art.

Buffer and viscosity aspects of the present invention will be further considered hereinafter.

It should be apparent that the combination of the volume of the composition and the concentration of nicotine in the composition provide the desired unit dosage of nicotine, which is according to the invention between about 0.5 to 5 mg per unit dose. In providing such dosages, it is a simple matter to calculate volume and concentration to end up with a dosage within the desired range. However, from a practical standpoint, it is frequently the case that all of a composition in a particular container, especially in a unit-dose container, is not ejected from the container upon use. In such case, compensation must be made by employment of increased volume so as to permit ejection and utilization of sufficient volume to provide a dose within the desired range. In point of fact, it has been found that, with a composition of the invention, depending on the viscosity involved, a considerable amount frequently does adhere to the inside of a unit-dose container and remains therein upon use and application. For this reason, it is frequently necessary to compensate by increasing the volume of the composition employed. Depending upon the nature and configuration of the unit-dose container involved, an increase in the volume of the composition in the container by as much as 200%, to ensure the desired dosage upon administration, has frequently been found desirable.

Such a situation is, of course, more pronounced at the lower volume ranges than at the higher volume ranges, since the amount dispensed from a particular container is as usual related to the amount of material in the container. Although excess volume is therefore recommended, to provide the desired dosage upon administration, it is pointed out that an excessively large dose of nicotine is definitely not recommended, so that the volume and the concentration are to be correlated with the amount dispensed in a unit-dose or from a disposable unit in order to provide a nicotine dosage within the prescribed range. Such relationships are simple calculations for one skilled in the art and acquainted with the normal correlations involved in the dispensation of compositions from unit- or multiple-dose containers.

It is to be noted that, according to previous investigators, who were concerned with the rapid absorption of nicotine in the buccal cavity, the solution of the nicotine should have an alkaline pH (A. H. Beckett et al, Journal of Pharmacy and Pharmacology 24: 115–120, 1972). Quite to the contrary of these investigators, our finding is that the pH of the compositions of the invention for our purpose must be maintained at relatively low pH-ranges, for reasons already stated, but also to avoid the extremely strong and disagreeable taste reactions which occur when the pH is even weakly alkaline.

Accordingly, the present invention provides a novel approach to a smoking substitute which is both socially-acceptable and quite unpredictably not only well-tolerated by the individual, but which also gives a satisfactory absorption, producing blood levels which are in fact similar to those obtained after cigarette smoking, so that a sense of nicotine satisfaction is obtained by a user who requires the same.

Viscosity

As will be noted, the compositions, i.e., the nicotine solutions of the invention, should have a viscosity not less than 100 cp. The reason for this viscosity requirement is so that the solution will adhere to the mucous membrane after introduction into the nasal cavity and will not produce excessive run-off through the nostril or, conversely, as already explained, into the buccal cavity. The necessary viscosity of 100 cp or above is readily obtained in numerous ways which will be readily understood by one skilled in the art. For example, physiologically- or nasally-acceptable thickening agents may be employed. These may be in the form of the usual thickening agents, or they may be in the form of the oil phase of an emulsion. Practically all the nicotine will remain in the aqueous phase of an emulsion, whether an oil-in-water or a water-in-oil emulsion is employed for purposes of obtaining the necessary viscosity.

Among the numerous thickening agents which are available in the art and nasally-acceptable may be mentioned the natural, semi-synthetic or synthetic polymers, examples of which are gum arabic, cellulose, methyl cellulose, and poly (ethylene oxide). Mixtures of such polymers may be employed if desired. Further representative thickening agents may be hydroxyethylcellulose, hydroxypropylcellulose, hydroxypropylmethylcellulose, or the like. Sodium and other salts of carboxymethylcellulose can also be used. Microcrystalline cellulose, which is practically insoluble in water, may be used to form a suspension. In contrast, the previously mentioned cellulose derivatives are soluble in water. Additional thickening agents may include polyvinylpyrrolidone, polyethylene glycol, and the like. Whether the thickening agent is a natural, a semi-synthetic, or a synthetic polymer, or a thickening agent of another type, it is only necessary that it be physiologically- and nasally-tolerable and that it be stable within the pH-ranges involved for the composition according to the present invention.

If an emulsion is employed for thickening purposes, as previously stated, this may be either an oil-in-water (o/w) or a water-in-oil (w/o) type. The oil phase of the emulsion may be any suitable mineral, animal, or vegetable oil, including, for example, paraffins, petrolatum, lanolin, beeswax, peanut oil, olive oil, castor oil, or the like. Innumerable oils and other materials which may constitute the oil phase of any particular emulsion are known in the art, and any of these may be employed with facility so long as they are physiologically- and nasally-acceptable and stable within the pH-ranges employed for the compositions of the present invention.

When emulsification is employed as the means of thickening a composition of the invention, an emulsifying agent is employed to advantage. When an emulsifying agent is employed, any emulsifying agent which is stable within the pH-ranges of the compositions of the invention and physiologically- and nasally-acceptable may be employed. In addition, emulsification may be employed as a means of thickening the compositions of the invention together with a thickening agent, which may be used in the water phase of such an emulsion. In such case, the foregoing named thickening agents may be employed for such purpose.

When an emulsifying agent is employed, it may be, for example, cholesterol, polyoxyethylene sorbitan fatty acid esters, polyoxyethylene fatty acid esters, sodium stearate, sodium lauryl sulphate, and the like.

Emulsifying agents of any type may be employed, but the non-ionic emulsifyers are preferred to the cationic and anionic types. Amphoteric emulsifying agents, such as lecithin, may also be used.

When thickening agents are employed and, whether they be normal thickening agents or whether the thickening be effected by emulsification, normal procedure in the art is employed. No particular problems are encountered. As stated in the foregoing, the viscosity of the compositions of the invention should be such as to maintain the composition, upon administration to the nasal passageway, in contact with the nasal mucosa for a sufficient period to permit absorption of the nicotine through the nasal mucosa into the bloodstream of the subject. For this purpose, the amount of the thickening agent, whatever type might be employed, should be such as to render the composition of sufficient viscosity so that it does not suffer from excessive run-off or deposit itself disadvantageously in the buccal cavity through the rear of the nasal passageway. From the standpoint of numerical values, the amount of thickening agent employed should be such as provides a viscosity not less than 100 cp, preferably not less than about 1000 cp, and preferably about 3000–4000 cp. At higher viscosities, as indicated previously and with particular reference to the drawings, the composition of the invention is advantageously dispensed in a unit-dose container or multi-dose container having a unit-dose neck and, upon placement into the container, maintains its position in the neck of the container until use. This is particularly advantageous inasmuch as it permits administration of a unit-dose into the nasal passageway in a convenient manner, and the viscosity of the composition thus not only maintains it in contact with the nasal mucosa for a sufficient period for absorption to occur, but also enables it to be conveniently delivered through the unit-dose container employed or by a corresponding multi-dose container having a unit-dose neck.

Buffering Agents

As already stated, at lower pH's the absorption of nicotine is relatively slow. The time it takes to increase the pH by the action of the normal physiological pH of the nasal mucosa, can be further prolonged by the employment of buffering agents in the nicotine solution. This is not always necessary, especially when the solution originally has a relatively low pH, i.e., a pH in the lower ranges specified according to the invention, for example 2–5. As already stated, the preferred pH-range is 3–5, and buffers which provide effective buffering effect within the range of 2–6 and preferably 4–6 are accordingly preferred. As will be readily understood, the presence of a buffer is more advantageous and desirable when the initial pH of the composition is relatively high in the acceptable range, for the reason that it is not desirable to have the solution pH climb too quickly by virtue of the action of the nasal mucosa into a more basic range, where tolerance is seriously reduced and untoward sensations are aggravated.

At the other end of the range, of course, for example at a pH of 4, where only about 0.01% of the nicotine is in the unprotonated absorbable form, and the other 99.9% exists as protonated nicotinium cations, the presence of a buffer is somewhat less important.

With respect to the buffer, when employed it is usually employed in an amount below about 5% by weight, most preferably between about 0.5 and 3% by weight, although in certain circumstances the amount of the buffer can even be higher, for example up to about 10% by weight.

As far as the physiologically- and nasally-acceptable buffering substances are concerned, numerous are available in the art and any of these may be employed. For example, inorganic water-soluble phosphates are particularly well adapted for use in the compositions of the invention. Other buffering agents which aay be employed with equal facility include citric acid, malic acid, lactic acid, succinic acid, tartaric acid, as mixtures with their water-soluble salts. Innnumerable other buffering substances which are physiologically- and nasally-acceptable are known in the art, and these may also be employed if desired.

Flavouring

If desired, the composition of the invention may also include a flavouring agent. This may be of any desired kind or type as long as it is physiologically- and nasally-acceptable and compatible with the other ingredients of the composition at the pH-ranges employed. Menthol is a particularly preferred flavouring agent, but numerous others may be employed, such as the usual essential oils, including oil of wintergreen, oil of peppermint, oil of clove, or oil of spearmint, or honey, figs, liquorice, vanilla, or the like.

When no flavouring agent is added, the composition of the invention is characterized by a slight nicotine odour, due to the non-ionized nicotine which, as previously indicated, will vary considerably from the lower to the higher pH-ranges involved in the composition of the invention.

Preservatives

A preservative may also optionally be present in the composition of the invention, and may be of any suitable type, provided only that it is physiologically- and nasally-acceptable and stable within the pH-ranges of the composition of the invention. The presence of a preservative is particularly advantageous when the pH of the solution is above about 4. Representative suitable preservatives include alkylparabens such as methyl paraben and propylparaben, benzoic acid, sorbic acid, chlorocresol, chlorohexidine, or the like. When a preservative is employed, it is generally employed in normal amounts, usually in a range between about 0.01 and 1.0%, generally on the order of 0.1% by weight.

Antioxidants

The composition of the invention may also contain an antioxidant which is compatible with the other ingredients and which is physiologically-and nasally-acceptable and stable under the pH conditions involved. Representative antioxidants include, among others, ascorbic acid, sodium bisulfite, butylated hydroxyanisole, butylated hydroxytoluenes, and the like. A considerable number of antioxidants have found wide use in foods, and any of the established antioxidants meeting the requirements as stated in the foregoing may be employed. When an antioxidant is employed in a composition of the invention, it is usually employed in an amount between about 0.001 and 1.0%, generally on the order of 0.01 to 0.1% by weight.

Innumerable flavourings, preservatives, and antioxidants are well known in the art, both in the pharmaceutical and in the food industry, and any of these type materials meeting the prescribed requirements of physiological acceptability and stability under the pH-ranges of the composition of the invention and being compatible with the other ingredients may be employed with facility.

DETAILED DESCRIPTION OF THE INVENTION

In the following examples the nicotine used is pure natural nicotine base or a salt thereof. The water used can be distilled or deionized. The viscosity of the solutions and emulsions is determined at room temperature with a rotational viscometer, Brookfield LVT, and is given in cp (centipoise) at 12 r. p. m. The volume of the final solution dispensed in the disposable unit-dose containers is calculated to give the dose of nicotine as mentioned in the example. In the multiple-dose containers the neck-portion is such that the dose of nicotine given is the one mentioned in the examples. The total volume of solution dispensed in the multiple-dose containers is about two-thirds of its volume.

The following Preparations and Examples are given by way of illustration only, and are not to be construed as limiting.

EXAMPLE 1

| | |
|---|---|
| Nicotine | 10 g |
| Sodium dihydrogen phosphate $NaH_2PO_4$, $H_2O$ | 10 g |
| Hydroxypropyl methylcellulose (Methocel E4M, TM) | 20 g |
| Hydrochloric acid ad pH 4 | |
| Water to make | 1000 ml |

The nicotine is dissolved in 500 ml of water together with the phosphate which is acting as a buffer. The pH is adjusted with a 5N HCl-solution.

The hydroxypropyl methylcellulose is dispersed in 300 ml of water at about 60° C.

The nicotine solution is added with stirring to the warm cellulose slurry, the mixture is allowed to cool, and the volume is made up with water to 1000 ml. The viscosity of the solution is found to be about 3900 cp.

The solution is dispensed in disposable single dose units or multiple-dose containers, which deliver a given dose of either 1 mg or 0,5 mg nicotine.

EXAMPLE 2

The procedure set forth in Example 1 is followed, but the amount of nicotine is replaced by 40 g, the amount of phosphate by 20 g and the pH is adjusted to 6.

To the composition is added menthol 80 mg as a flavouring agent, ascorbic acid 1 g as an antioxidant and methyl para-hydroxybenzoate 1 g as a preservative.

The viscosity is found to be about 3800 cp. The solution is dispensed as in Example 1 so that the given dose is either 4 mg or 2 mg nicotine.

EXAMPLE 3

The procedure set forth in Example 1 is followed, but the amount of nicotine is replaced by 50 g and the amount of phosphate by 30 g.

To the composition is added oil of peppermint 1 g. The viscosity is found to be about 3900 cp. The solution is dispensed as in Example 1 so that the given dose is either 5 mg or 2.5 nicotine.

EXAMPLE 4

The procedure set forth in Example 1 is followed, but the amount of nicotine is replaced by 100 g, the phosphate is excluded, and the pH is adjusted to 2.

To the composition is added oil of wintergreen 1 g and butylated hydroxyanisole 0.1 g. The viscosity is found to be about 3600 cp. The solution is dispensed as in Example 1 so that the given dose is 5 mg nicotine.

EXAMPLE 5

The procedure set forth in Example 1 is followed, but the amount of nicotine is replaced by 20 g and the sodium dihydrogen phosphate by sodium monohydrogen phosphate, $Na_2HPO_4, 2H_2O$, 10 g.

The viscosity is found to be about 3900 cp.

The solution is dispensed as in Example 1 so that the given dose is either 2 mg or 1 mg nicotine.

EXAMPLE 6

The procedure set forth in Example 1 is followed, but the addition of phosphate is excluded. The viscosity is found to be about 4000 cp. The solution is dispensed as in Example 5.

EXAMPLE 7

The procedure set forth in Example 1 is followed, but the addition of phosphate is excluded, the pH adjusted to about 5, sodium bisulfite 1 g added as an antioxidant, sodium benzoate 1 g as a preservative, and vanilla 1 g as a flavouring agent.

The viscosity is found to be about 4000 cp.

The solution is dispensed as in Example 5.

EXAMPLE 8

The procedure set forth in Example 1 is followed, but the amount of hydroxypropyl methylcellulose is replaced by 22 g.

The viscosity of the solution is found to be about 5900 cp. The solution is dispensed as in Example 1.

EXAMPLE 9

The procedure set forth in Example 1 is followed, but the amount of hydroxypropyl methylcellulose is replaced by 18 g.

The viscosity is found to be about 3000 cp.

The solution is dispensed as in Example 1.

EXAMPLE 10

The procedure set forth in Example 1 is followed, but the amount of hydroxypropyl methylcellulose is replaced by 16 g.

The viscosity is found to be about 1900 cp.

The solution is dispensed as in Example 1.

EXAMPLE 11

The procedure set forth in Example 1 is followed, but the amount of hydroxypropyl methylcellulose is replaced by 14 g.

The viscosity is found to be about 1200 cp.

The solution is dispensed as in Example 1.

EXAMPLE 12

The procedure set forth in Example 1 is followed, but the hydroxypropyl methylcellulose is replaced by 20 g of hydroxypropyl cellulose (Klucel MF, TM).

The viscosity is found to be about 4 200 cp.

The solution is dispensed as in Example 1.

EXAMPLE 13

The procedure set forth in Example 1 is followed, but the hydroxypropyl methylcellulose is replaced by poly(ethylene oxide) (Polyox WSR-301, TM) 15 g.

The viscosity is found to be about 3200 cp.

The solution is dispensed as in Example 1.

EXAMPLE 14

| | |
|---|---|
| Nicotine | 10 g |
| Sodium dihydrogen phosphate $NaH_2PO_4$, $H_2O$ | 5 g |
| A mixture of microcrystalline cellulose and sodium carboxymethyl cellulose (Avicel RC 591, TM) | 20 g |
| Sorbic acid | 5 g |
| Hydrochloric acid ad pH 6 | |
| Water to make | 1000 ml |

Avicel RC 591, TM is dispersed in 800 ml of water. The dispersion is treated by a colloidal mill, type Collovelox. In the dispersion the nicotine is dissolved together with the phosphate, which is acting as a buffer, and the sorbic acid as a preservative agent.

The pH is adjusted to 6 with 5 N HCl and the volume is made up to 1000 ml with water.

The viscosity of the resulting solution is found to be about 2000 cp.

The solution is dispensed in disposable single dose units or multiple-dose containers, which deliver a given unit dose of either 1 mg or 0.5 mg nicotine.

EXAMPLE 15

| | |
|---|---|
| Nicotine | 20 g |
| Sodium dihydrogen phosphate $NaH_2PO_4$, $H_2O$ | 20 g |
| Sodium carboxymethyl cellulose (Cellugel 3000, TM) | 21 g |
| Hydrochloric acid ad pH 4 | |
| Water to make | 1000 ml |

The nicotine is dissolved in 900 ml of water together with the phosphate which is acting as a buffer. The sodium carboxymethyl cellulose is added and dissolved by stirring. The pH is adjusted to about 4 with 5N HCl.

The volume is made up to 1000 ml with water. The viscosity is found to be about 1800 cp.

The solution is dispensed in disposable single dose units or multiple-dose containers, which deliver a given unit dose of either 2 mg or 1 mg nicotine.

EXAMPLE 16

The procedure set forth in Example 15 is followed, but the sodium carboxymethyl cellulose is replaced by 30 g of methyl cellulose (Methocel A4M, TM).

The viscosity is found to be about 4500 cp.

The solution is dispensed as in Example 15.

EXAMPLE 17

The procedure set forth in Example 15 is followed, but the sodium carboxymethyl cellulose is replaced by 15 g of hydroxyethyl cellulose (Cellosize QP 4400, TM).

The viscosity is found to be about 3500 cp.

The solution is dispensed as in Example 15.

EXAMPLE 18

| | |
|---|---|
| Nicotine | 20 g |
| Tartaric acid (natural acid) | 15 g |
| Hydroxypropyl methylcellulose (Methocel E4M, TM) | 20 g |
| Water to make | 1000 ml |

The nicotine is dissolved in 500 ml of water together with the tartaric acid.

The hydroxypropyl methylcellulose is dispersed in 300 ml of water at about 60° C. The nicotine solution is added with stirring to the warm cellulose slurry and the mixture is allowed to cool.

The volume is made up to 1000 ml with water. The pH of the solution is found to be about 4.

The viscosity of the solution is found to be about 3900 cp.

The solution is dispensed in disposable single dose units or multiple-dose containers, which deliver a given unit dose of either 2 mg or 1 mg nicotine.

EXAMPLE 19

The procedure set forth in Example 18 is followed, but the tartaric acid is replaced by 12.3 g succinic acid.

The pH is found to be about 5.
The viscosity is found to be about 3800 cp.
The solution is dispensed as in Example 18.

EXAMPLE 20

The procedure set forth in Example 18 is followed, but the tartaric acid is replaced by 26.3 g lactic acid (90%).

The pH is found to be about 4.
The viscosity is found to be about 3900 cp.
The solution is dispensed as in Example 18.

EXAMPLE 21

The procedure set forth in Example 18 is followed, but the tartaric acid is replaced by 12.9 g citric acid.

The pH is found to be about 5.
The viscosity is found to be about 3800 cp.
The solution is dispensed as in Example 18.

EXAMPLE 22

The procedure set forth in Example 18 is followed, but the amount of tartaric acid is replaced by 25 g.

The pH is adjusted to about 4 with 5N NaOH, which means that in the solution about 10 g of the tartaric acid constitute a buffer.

The viscosity is found to be about 3900 cp.
The solution is dispensed as in Example 18.

EXAMPLE 23

The procedure set forth in Example 18 is followed, but the tartaric acid is replaced by 32.3 g succinic acid.

The pH is adjusted to about 5 with 5N NaOH, which means that in the solution about 20 g of the succinic acid constitute a buffer.

The viscosity is found to be about 3800 cp.
The solution is dispensed as in Example 18.

EXAMPLE 24

The procedure set forth in Example 18 is followed, but the tartaric acid is replaced by 56.3 g lactic acid (90%).

The pH is adjusted to about 4 with 5N NaOH, which means that in the solution about 30 g of the lactic acid constitute a buffer.

The viscosity is found to be about 3900 cp.
The solution is dispensed as in Example 18.

EXAMPLE 25

The procedure set forth in Example 18 is followed, but the tartaric acid is replaced by 42.9 g citric acid.

The pH is adjusted to about 5 with 5N NaOH, which means that in the solution about 30 g of the citric acid constitute a buffer.

The viscosity is found to be about 3800 cp.
The solution is dispensed as in Example 18.

EXAMPLE 26

| | |
|---|---|
| Nicotine hydrogen (+) tartrate, $C_{10}H_{14}N_2(C_4H_6O_6)_2$, $2H_2O$ (corresponding to 20 g nicotine base) | 61.44 g |
| Hydroxypropyl methylcellulose (Methocel E4M, TM) | 20 g |
| Water to make | 1000 ml |

The nicotine salt is dissolved in 500 ml of the water.

The hydroxypropyl methylcellulose is dispensed in 300 ml of water at about 60° C. The nicotine solution is added with stirring to the warm cellulose slurry, the mixture is allowed to cool, and the volume is made up to 1000 ml with water.

The pH of the solution is found to be about 3 and the viscosity to be about 3700 cp.

The solution is dispensed in disposable single dose units or multiple-dose containers, which deliver a given unit dose of either 2 mg or 1 mg nicotine.

EXAMPLE 27

The procedure set forth in Example 26 is followed, but the nicotine hydrogen (+) tartrate is replaced by 42.96 g of nicotine (+) tartrate, $C_{10}H_{14}N_2$, $C_4H_6O_6$, $2H_2O$, corresponding to 20 g nicotine base.

The pH of the solution is adjusted to about 4 with tartaric acid.

Its viscosity is found to be about 3900 cp.
The solution is dispensed as in Example 26.

EXAMPLE 28

The procedure set forth in Example 26 is followed, but the nicotine hydrogen (+) tartrate is replaced by 24.5 g nicotine hydrochloride, $C_{10}H_{14}N_2$, HCl, corresponding to 20 g nicotine base.

The pH of the solution is adjusted to about 4 with 5N HCl.

Its viscosity is found to be about 3900 cp.
The solution is dispensed as in Example 26.

EXAMPLE 29

The procedure set forth in Example 26 is followed, but the nicotine hydrogen (+) tartrate is replaced by 29 g nicotine dihydrochloride, $C_{10}H_{14}N_2$, 2HCl, corresponding to 20 g nicotine base.

The pH of the solution is about 3.
Its viscosity is found to be about 3700 cp.
The solution is dispensed as in Example 26.

EXAMPLE 30

The procedure set forth in Example 26 is followed, but the nicotine hydrogen (+) tartrate is replaced by 52.1 g nicotine sulphate, $(C_{10}H_{14}N_2)_2$, $H_2SO_4$, corresponding to 20 g nicotine base.

The pH of the solution is about 3.
Its viscosity is found to be about 3700 cp.
The solution is dispensed as in Example 26.

EXAMPLE 31

| | | |
|---|---|---|
| A. | Nicotine | 20 g |
| | Sodium dihydrogen phosphate, $NaH_2PO_4$, $H_2O$ | 15 g |
| | Hydrochloric acid ad pH 4 | |
| | Water ad | 785 g |
| | Petrolatum | 42.5 g |

|   | | |
|---|---|---|
| B. | White wax | 30 g |
|   | Lanolin anhydride | 22.5 g |
|   | Sorbitan sesquioleate (Arlacel 83, TM) | 20 g |
|   | Mineral oil | 100 g |

A is mixed and the solution obtained is heated to about 70° C.

B is melted and mixed at about 70° C.

B is then added to A with continous agitation and cooling to room temperature.

The viscosity of the resulting w/o-emulsion is found to be 1400 cp. It is dispensed in disposable single dose units or multiple-dose containers which deliver a given unit dose of either 2 mg or 1 mg nicotine.

EXAMPLE 32

|   | | |
|---|---|---|
| A. | Nicotine | 20 g |
|   | Tartaric acid | 25 g |
|   | Sodium hydroxide ad pH 4 | |
|   | Propylene glycol | 10 g |
|   | Sorbitol 70% | 40 g |
|   | Water ad | 710 g |
| B. | Mineral oil | 170 g |
|   | Isopropylmyristate | 50 g |
|   | White wax | 10 g |
|   | Polyoxyethylene sorbitan trioleate (Tween 85, TM) | 30 g |
|   | Sorbitan sesquioleate (Arlacel 83, TM) | 30 g |

A is mixed and the pH of the solution obtained is adjusted to about 4 with 5N NaOH, which means that in the solution about 10 g of the tartaric acid constitute a buffer. The solution is heated to 70° C.

B is melted and mixed at 70° C.

B is then added to A with continous agitation and cooling to room temperature.

The viscosity of the resulting o/w-emulsion is found to be about 2200 cp.

It is dispensed in disposable single dose units or multiple-dose containers, which deliver a given unit dose of either 2 mg or 1 mg nicotine.

EXAMPLE 33

| | |
|---|---|
| Nicotine | 10 g |
| Tartaric acid (natural acid) | 10 g |
| Polyethylene glycol 4000 | 100 g |
| Hydroxyethyl cellulose (Cellosize QP 4400) | 17 g |
| Sorbic acid | 1 g |
| Flavouring mixture | 0.6 g |
| Water to make | 1000 ml |
| pH adjusted to 5 with sodium hydroxide | |

The nicotine is dissolved in 500 ml of water together with the tartaric acid.

The hydroxyethyl cellulose is dispersed in 300 ml of water at about 60° C. The nicotine solution is added with stirring to the warm cellulose slurry and the mixture is allowed to cool.

Administration and Pharmacology

The administration of a composition of the invention to a subject as a substitute for smoking comprises the step of applying to the nasal mucosa in the nasal cavity of the subject a composition according to the invention. This is effected without difficulty. The subject simply maintains his head in an upright position, in preference to a backwardly-tilted position, to avoid unnecessary entry of the composition into the buccal cavity through the rear of the nasal passageway. Upon exerting pressure upon the pressure-application chamber of a unit-dose container in which the composition of the invention is contained, preferably in the nasally-insertable neck thereof, the unit-dose is conveniently expelled into the nasal passageway and into contact with the nasal mucosa. Of course, when the composition is so packaged, the unit-dose container is usually initially closed by a small plastic appendage which must be removed prior to administration, as is normal in the art. When the composition of the invention is packaged in a multi-dose container having a unit-dose neck, the same procedure is employed. Of course, other ways of administration may be utilized, such as the employment of a dropper, syringe, or the like, but administration in a unit-dose container according to the foregoing description constitutes a preferred mode of packaging and operation according to the invention. After waiting a short time, generally less than ten minutes, the blood levels of the subject will rise substantially and the nicotine content, after administration of a 2 mg nicotine single unit dose, will attain a level between 10 and 20 ng, about equivalent to the blood levels obtained upon smoking a normal cigarette (see O. Fernö in World Smoking & Health 5 (1980) 24–29). Substantial or habitual smokers experience a feeling of smoking satisfaction upon administration of a composition of the invention and, of course, administration to subjects in need of such administration or desiring the same is accomplished with facility, even though they may be denture wearers.

Proceeding according to the method of administration of the present invention, any of the compositions of the foregoing examples may be employed. They are found to be well tolerated, particularly at the lower pH-levels and, especially when a buffering agent is present therein, even at higher pH-levels. The viscosity maintains the composition in contact with the nasal mucosa for an adequate period for absorption to occur.

Representative tests upon substantial or habitual smoking subjects were carried out employing compositions of the foregoing examples.

In such a test upon occasional cigar smokers using compositions of the foregoing examples, namely, of examples 5 and 6, the following blood levels were obtained upon administration to the nasal mucosa of the two subjects involved in a single unit dose of 2 mg nicotine (0.1 ml).

| Time after administration of the composition in minutes | Blood level of nicotine (ng/ml) found with 2 mg nicotine of the composition of | |
|---|---|---|
| | Example 6 Subject 1 | Example 5 Subject 2 |
| 1 | 1.0 | 1.3 |
| 2.5 | 7.3 | 2.4 |
| 5 | 16.0 | 4.1 |
| 7.5 | 14.7 | 8.5 |
| 10 | 14.4 | 15.8 |
| 15 | 11.1 | 13.1 |
| 20 | 9.8 | 10.3 |
| 30 | 7.3 | 7.7 |
| 45 | 7.2 | 6.1 |
| 60 | 5.8 | 4.9 |

The blood levels of nicotine before the experiment started were below 1 ng/ml in both subjects.

As seen from the figures above an effective blood level of approximately 16 ng/ml of nicotine was obtained within 5 and 10 minutes, respectively, and the blood levels of both of the subjects involved evidence that the compositions of the invention do in fact provide nicotine blood levels approximately equivalent to those obtained upon the smoking of a normal cigarette. In both cases, the subjects not only experienced the elevated nicotine blood levels, but found it possible to abstain from smoking during an extended period after administration.

What we claim is:

1. A smoking substitute composition for application directly into the nose, consisting essentially of an aqueous solution of nicotine or a physiologically acceptable acid addition salt thereof, having a pH value of 2 to 6, containing 10 to 0.5% w/v of nicotine calculated as the free base, containing a nasally-acceptable thickening agent, having a viscosity not less than 100 centipose, and having about 0.5 to 5 mg nicotine per every 0.05 to 0.5 ml thereof.

2. A composition of claim 1 in a unit dosage form comprising 0.05 up to 0.5 ml of said aqueous solution which delivers about 0.5 to 5 mg nicotine per unit dose.

3. A composition of claim 1, having a viscosity not less than 1,000 centipoise.

4. A composition of claim 3, containing an effective amount of nasally-acceptable buffer having a buffering effect in the range of pH 2 to 6.

5. A composition of claim 4, wherein the buffer has a buffering effect in the range of pH 4 to 6.

6. A composition of claim 3, having a viscosity not higher than 6,000 centipoise.

7. A composition of claim 1, wherein the thickening agent is a nasally-acceptable natural or synthetic polymer.

8. A composition of claim 1, wherein the thickening agent is a nasally-acceptable oily substance constituting the oil-phase of an emulsion.

9. A composition of claim 8, also comprising an emulsifying agent.

10. A composition of claim 1, having a pH value of 3 to 5.

11. A composition of claim 1, containing 5 to 1% w/v of nicotine.

12. A composition of claim 11, containing 4 to 2% w/v of nicotine.

13. A composition of claim 1, wherein the aqueous solution is 0.05 up to 0.3 ml.

14. A composition of claim 1, containing also an effective amount of a nasally-acceptable preservative agent.

15. A composition of claim 1, containing also an effective amount of a nasally-acceptable flavoring agent.

16. A composition of claim 1, containing also an effective amount of a nasally-acceptable antioxidant.

17. A composition of claim 2, wherein the composition is in unit dosage form in a disposable plastic container having a nostril-insertable neck portion of restrictive volume adjacent to an emission opening and a pressure-application chamber of a relatively larger volume in communication with said neck portion, wherein the said composition is disposed in said neck portion and of sufficient viscosity to retain said location until the time of application.

18. A composition of claim 17, wherein the nostril-insertable container neck is itself dimensioned so as to contain a unit dose and wherein a squeeze-bottle container constitutes the relatively larger pressure application chamber, the unit dose neck thus constituting a portion of a multi-dose container.

19. A method of diminishing the desire of a subject to smoke, which comprises the step of administering to the subject intranasally a smoking substitute composition according to any one of claims 1 through 18.

* * * * *

UNITED STATES PATENT AND TRADEMARK OFFICE
CERTIFICATE OF CORRECTION

PATENT NO. : 4,579,858

DATED : April 1, 1986

INVENTOR(S) : Ove B. Fernö, Stig K. A. Helgertz and Corfitz B. I. Ohlsson

It is certified that error appears in the above-identified patent and that said Letters Patent is hereby corrected as shown below:

Col. 1, line 39; before "gum" insert -- a --
Col. 1, line 55; "tn" should read -- to --
Col. 2, line 30; "inrrease" should read -- increase --
Col. 2, line 46; "proceeeded" should read -- proceeded --
Col. 7, line 29; "acidid" should read -- acidic --
Col. 11, line 6; "aay" should read -- may --
Col. 11, line 9; "Innnumerable" should read -- Innumerable --
Col. 13, line 60; "4 200" should read -- 4200 --
Col. 16, line 68; the "ad" after "water" should be before "785 g" to read -- ad 785 g --
Col. 16, last line; the last line "Petrolatum    42.5 g" should be in the bracket "B.", on the next page, Col. 17, the Table-continued of Example 31.
Col. 17, approximately line 23 1/2; the "ad" after "water" should be before "710 g" to read -- ad 710 g --
Col. 19, line 16; "centipose," should read -- centipoise, --
Col. 19, line 19; insert a comma -- , -- after "claim 1"
Col. 20, line 18; "claim 2," should read -- claim 1, --
Col. 20, lines 30&31; "pressure application" should read -- pressure-application --

Signed and Sealed this

Ninth Day of September 1986

[SEAL]

Attest:

DONALD J. QUIGG

Attesting Officer

Commissioner of Patents and Trademarks